(12) United States Patent
Hasegawa et al.

(10) Patent No.: US 11,088,207 B2
(45) Date of Patent: Aug. 10, 2021

(54) SOLID-STATE IMAGE SENSOR, PHOTOELECTRIC CONVERSION FILM, ELECTRON BLOCKING LAYER, IMAGING APPARATUS, AND ELECTRONIC DEVICE

(71) Applicant: SONY SEMICONDUCTOR SOLUTIONS CORPORATION, Kanagawa (JP)

(72) Inventors: Yuta Hasegawa, Kanagawa (JP); Nobuyuki Matsuzawa, Tokyo (JP); Daisuke Hobara, Kanagawa (JP); Atsushi Wakamiya, Kyoto (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 84 days.

(21) Appl. No.: 15/577,319

(22) PCT Filed: May 25, 2016

(86) PCT No.: PCT/JP2016/065386
§ 371 (c)(1),
(2) Date: Nov. 27, 2017

(87) PCT Pub. No.: WO2016/194717
PCT Pub. Date: Dec. 8, 2016

(65) Prior Publication Data
US 2018/0151625 A1    May 31, 2018

(30) Foreign Application Priority Data

Jun. 5, 2015  (JP) .............................. JP2015-114526
May 16, 2016  (JP) .............................. JP2016-098292

(51) Int. Cl.
| C07D 498/06 | (2006.01) |
| C07D 498/16 | (2006.01) |
| C07F 7/08 | (2006.01) |
| H01L 27/146 | (2006.01) |
| H01L 27/28 | (2006.01) |
| H01L 27/30 | (2006.01) |
| H01L 51/00 | (2006.01) |
| H01L 51/42 | (2006.01) |

(52) U.S. Cl.
CPC .......... *H01L 27/307* (2013.01); *C07D 498/06* (2013.01); *C07D 498/16* (2013.01); *C07F 7/0812* (2013.01); *H01L 27/1467* (2013.01); *H01L 27/14647* (2013.01); *H01L 27/286* (2013.01); *H01L 51/0067* (2013.01); *H01L 51/0071* (2013.01); *H01L 27/1464* (2013.01); *H01L 51/008* (2013.01); *H01L 51/0072* (2013.01); *H01L 51/0094* (2013.01); *H01L 51/4273* (2013.01)

(58) Field of Classification Search
CPC ............... H01L 27/307; H01L 27/1467; H01L 27/14647; H01L 51/0067; H01L 51/0071; H01L 27/286; H01L 51/008; H01L 51/0072; H01L 27/1464; H01L 51/4273; H01L 51/0094; C07D 498/16; C07D 498/06; C07F 7/0812

See application file for complete search history.

(56) References Cited

U.S. PATENT DOCUMENTS

| 2013/0228768 A1 | 9/2013 | Abe et al. |
| 2014/0058099 A1* | 2/2014 | Wakamiya ........... C07D 519/00 544/35 |

(Continued)

FOREIGN PATENT DOCUMENTS

| AU | 2014206925 A1 | 7/2015 |
| CN | 103502252 A | 1/2014 |

(Continued)

OTHER PUBLICATIONS

International Search Report and Written Opinion of PCT Application No. PCT/JP2016/065386, dated Aug. 16, 2016, 10 pages of ISRWO.

Nishimura, et al., "Hole-Transporting Materials with a Two-Dimensionally Expanded π-System around an Azulene Core for Efficient Perovskite Solar Cells", Journal of the American Chemical Society, vol. 137, No. 50, Dec. 23, 2015, pp. 15656-15659.

(Continued)

*Primary Examiner* — Amanda L. Aguirre
(74) *Attorney, Agent, or Firm* — Chip Law Group

(57) ABSTRACT

The present technology relates to a solid-state image sensor, a photoelectric conversion film, an electron blocking layer, an imaging apparatus, and an electronic device that can appropriately photoelectrically convert light of specific wavelengths with high spectral characteristics and high photoelectric conversion efficiency. A photoelectric conversion layer or an electron blocking layer is configured with a photoelectric conversion film made of only a compound represented by Chemical Formula (1).

[Chem. 1]

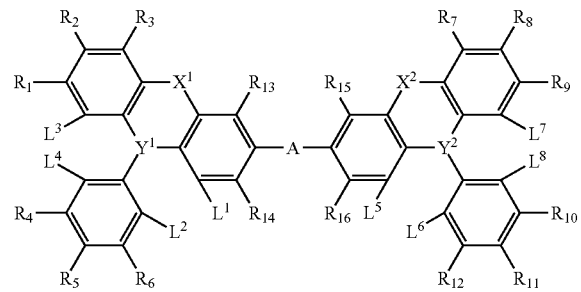

Chemical Formula (1)

The present technology can be applied to a solid-state image sensor.

9 Claims, 7 Drawing Sheets

(56) References Cited

U.S. PATENT DOCUMENTS

| | | | |
|---|---|---|---|
| 2014/0158859 A1* | 6/2014 | Fukuzaki | H01L 51/0056 250/200 |
| 2015/0333275 A1 | 11/2015 | Wonneberger et al. | |
| 2017/0183360 A1* | 6/2017 | Ishii | H01L 51/0071 |

FOREIGN PATENT DOCUMENTS

| | | | |
|---|---|---|---|
| CN | 104919613 A | 9/2015 | |
| EP | 2646447 A1 | 10/2013 | |
| EP | 2946420 A1 | 11/2015 | |
| JP | 2007-335760 A | 12/2007 | |
| JP | 2012-116794 A | 6/2012 | |
| JP | 2012116794 A * | 6/2012 | C07D 519/00 |
| JP | 2013-118335 A | 6/2013 | |
| KR | 10-2013-0098413 A | 9/2013 | |
| KR | 10-2015-0113014 A | 10/2015 | |
| WO | 2012/073679 A1 | 6/2012 | |
| WO | 2014/111365 A1 | 7/2014 | |

OTHER PUBLICATIONS

Office Action for CN Patent Application No. 201680030989.8, dated May 6, 2021, 13 pages of English Translation and 11 pages of Office Action.

* cited by examiner

FIG. 3

| | COMPOUND 1 | COMPOUND 2 | COMPOUND 3 | COMPOUND 4 |
|---|---|---|---|---|
| STRUCTURE | (structure) | (structure) | (structure) | (structure) |
| $\lambda_{max}$ (nm) | 374 | 407 | 409 | 372 |
| OPTICAL MICROSCOPIC OBSERVATION | COHESION | COHESION | COHESION | COHESION |
| EQE (P:N=1:1) | 12% (SPECTRAL SHAPE: BROAD) | NA | NA | NA |

| | COMPOUND 5 | COMPOUND 6 | COMPOUND 7 | COMPOUND 8 | COMPOUND 9 |
|---|---|---|---|---|---|
| STRUCTURE | (structure) | (structure) | (structure) | (structure) | (structure) |
| $\lambda_{max}$ (nm) | 388 | 382 | 394 | 385 | 380 |
| OPTICAL MICROSCOPIC OBSERVATION | NO CHANGE | NO CHANGE | NO CHANGE | NO CHANGE | NO CHANGE |
| EQE (P:N=1:1) | 7% | NA | NA | NA | NA |

SOLID-STATE IMAGE SENSOR, PHOTOELECTRIC CONVERSION FILM, ELECTRON BLOCKING LAYER, IMAGING APPARATUS, AND ELECTRONIC DEVICE

This application is a U.S. National Phase of International Patent Application No. PCT/JP2016/065386 filed on May 25, 2016, which claims priority benefit of Japanese Patent Application No. JP 2015-114526 filed in the Japan Patent Office on Jun. 5, 2015, and also claims priority benefit of Japanese Patent Application No. JP 2016-098292 filed in the Japan Patent Office on May 16, 2016.

TECHNICAL FIELD

The present technology relates to a solid-state image sensor, a photoelectric conversion film, an electron blocking layer, an imaging apparatus, and an electronic device, and relates particularly to a solid-state image sensor, a photoelectric conversion film, an electron blocking layer, an imaging apparatus, and an electronic device having high spectral characteristics, high photoelectric conversion characteristics, and high heat resistance.

BACKGROUND ART

A vertical spectral imager from which high color reproducibility is required, called a vertical spectral solid-state image sensor, is eagerly awaited. To this end, not only high photoelectric conversion characteristics but also high selective spectral properties are needed.

As the vertical spectral solid-state image sensor, one using a silicon (Si) material is known.

However, in a vertical spectral solid-state image sensor using a silicon material, the light absorption coefficient is small and therefore the film thickness needs to be thick; consequently, with extreme decrease in the area of the pixel, there are limitations on the spectral characteristics due to cross leakage, etc.

Thus, these days, a vertical spectral solid-state image sensor having a multiple-layer structure in which photoelectric conversion films formed of an organic material are stacked is proposed.

For example, there is disclosed a solid-state image sensor in which organic photoelectric conversion films that absorb blue light, green light, and red light, respectively, are stacked in order (see Patent Literature 1). In the solid-state image sensor disclosed in Patent Literature 1, light corresponding to each color is photoelectrically converted in each organic photoelectric conversion film, and thereby a signal of each color is extracted.

Further, there is disclosed a solid-state image sensor in which an organic photoelectric conversion film that absorbs green light and silicon photodiodes are stacked in order (see Patent Literature 2). In the solid-state image sensor disclosed in Patent Literature 2, a signal of green light is extracted by the organic photoelectric conversion film, and signals of blue light and red light that are separated using a difference in light entry depth are extracted by the silicon photodiodes.

CITATION LIST

Patent Literature

Patent Literature 1: JP 2003-234460A
Patent Literature 2: JP 2005-303266A

DISCLOSURE OF INVENTION

Technical Problem

However, in both organic photoelectric conversion films of Patent Literatures 1 and 2 described above, it is impossible to make photoelectric conversion while sufficiently making selective spectral analysis of light of each color.

Further, to fabricate a solid-state image sensor using an organic photoelectric conversion film, a heat treatment process for several hours in temperature conditions of more than 150° C. is required. If, for example, the film quality is changed by the heating, it is feared that a target function cannot be exhibited.

The present technology has been made in view of such circumstances, and particularly provides a photoelectric conversion film that has high spectral characteristics and high photoelectric conversion characteristics for light of specific wavelengths and further has high heat resistance.

Solution to Problem

According to an aspect of the present technology, a solid-state image sensor includes: a compound represented by Chemical Formula (1) below,

[Chem. 1]

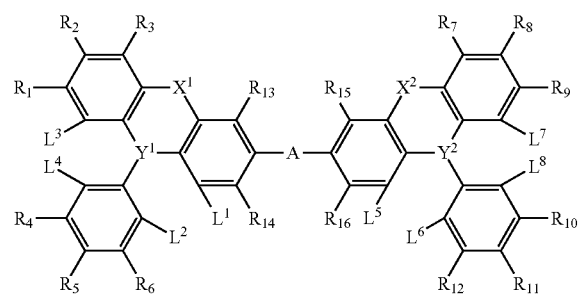

Chemical Formula (1)

in which, in the Chemical Formula (1), A is a compound formed of an aryl group or a heteroaryl group, Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

The A may have a molecular weight larger than 75.

A compound represented by the Chemical Formula (1) may have a molecular weight larger than 620.

A compound represented by the Chemical Formula (1) may have a molecular weight smaller than 1000.

The A may include compounds of Chemical Formula (3) to Chemical Formula (6) below,

[Chem. 3]

Chemical Formula (3)

[Chem. 4]

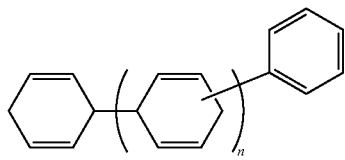

Chemical Formula (4)

[Chem. 5]

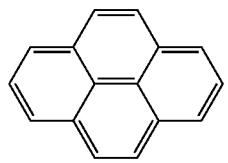

Chemical Formula (5)

[Chem. 6]

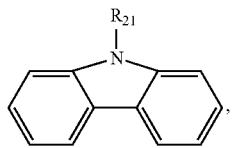

Chemical Formula (6)

B of the Chemical Formula (3) is different from A in Chemical Formula (1), and each represents a carbon atom or a nitrogen atom, n in the Chemical Formula (4) is n=1 to 5, and R21 of the Chemical Formula (6) may be aryl group or a heteroaryl group.

The compound represented by the Chemical Formula (1) may include a compound of Chemical Formula (9) below,

[Chem. 9]

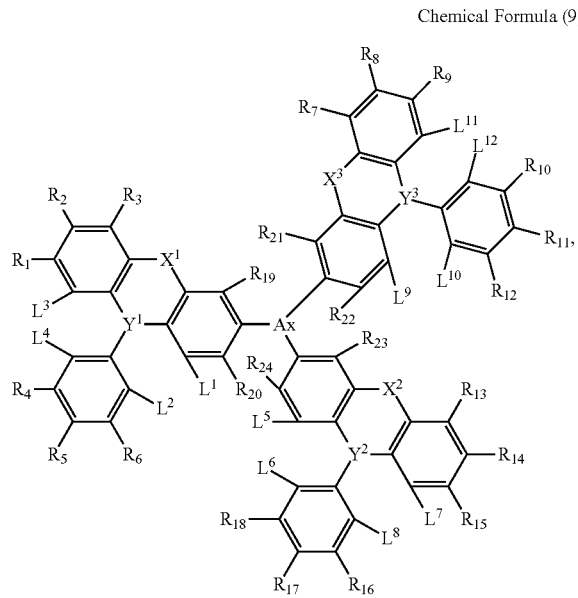

Chemical Formula (9)

Ax of the Chemical Formula (9) is represented by Chemical Formula (3) below,

[Chem. 3]

Chemical Formula (3)

and

B of the Chemical Formula (3) is different from A in Chemical Formula (1), and each may represent a carbon atom or a nitrogen atom.

A layer stacked between a pair of electrodes may be configured with a compound of the Chemical Formula (1).

The solid-state image sensor may further include, between the pair of electrodes: a photoelectric conversion layer configured to photoelectrically convert incident light; and an electron blocking layer configured to block an electron for the photoelectric conversion layer. The electron blocking layer may be configured with a compound of the Chemical Formula (1).

The photoelectric conversion layer may photoelectrically convert green light.

According to an aspect of the present disclosure, a photoelectric conversion film includes: a compound represented by Chemical Formula (1) below,

[Chem. 1]

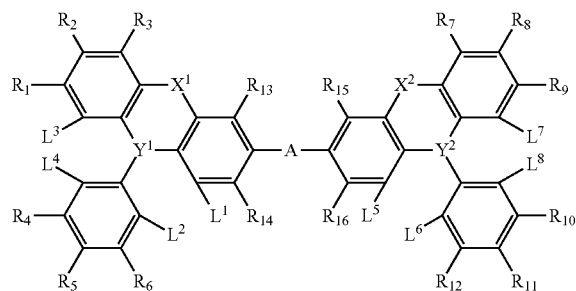

Chemical Formula (1)

in which, in the Chemical Formula (1), A is a compound formed of an aryl group or a heteroaryl group, Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

According to an aspect of the present disclosure, an electron blocking layer includes: a compound represented by Chemical Formula (1) below,

[Chem. 1]

Chemical Formula (1)

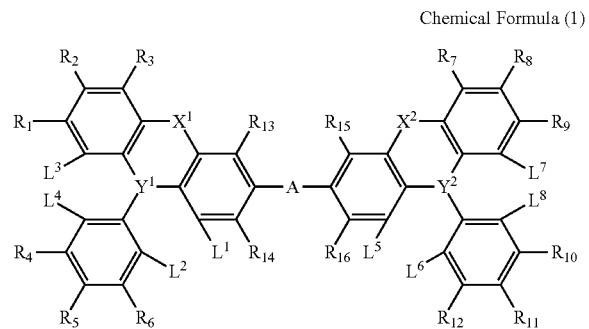

in which, in the Chemical Formula (1), A is a compound formed of an aryl group or a heteroaryl group, Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

According to an aspect of the present disclosure, an imaging apparatus includes: a compound represented by Chemical Formula (1) below,

[Chem. 1]

Chemical Formula (1)

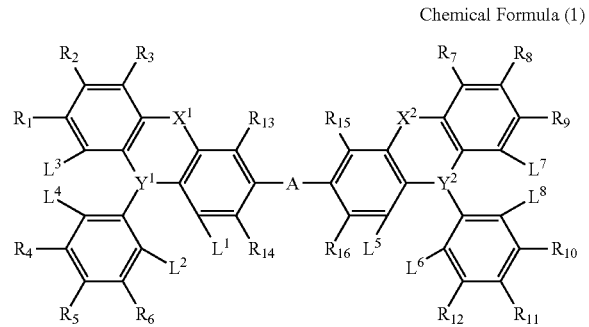

in which, in the Chemical Formula (1), A is a compound formed of an aryl group or a heteroaryl group, Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

According to an aspect of the present disclosure, an electronic device includes: a compound represented by Chemical Formula (1) below,

[Chem. 1]

Chemical Formula (1)

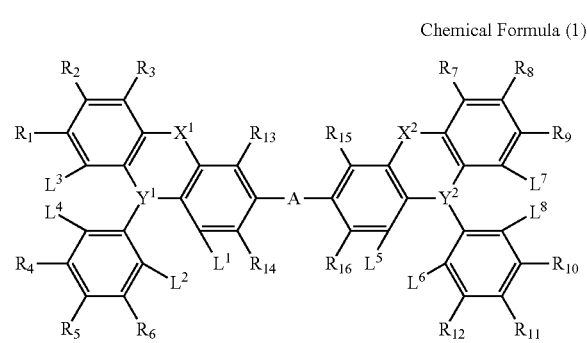

in which, in the Chemical Formula (1), A is a compound formed of an aryl group or a heteroaryl group, Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

In an aspect of the present disclosure, a compound represented by Chemical Formula (1) below is included.

[Chem. 1]

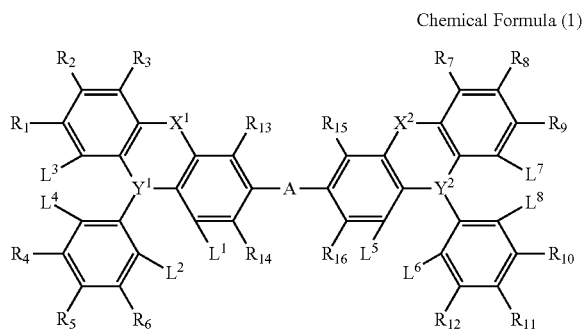

Chemical Formula (1)

Advantageous Effects of Invention

According to an aspect of the present technology, it becomes possible to provide a solid-state image sensor including a photoelectric conversion film that can photoelectrically convert light of specific wavelengths with high selectivity and high photoelectric conversion efficiency and has heat resistance.

BRIEF DESCRIPTION OF DRAWINGS

FIG. 3 is a diagram describing examples of the compound.

MODE(S) FOR CARRYING OUT THE INVENTION

<Overview of Photoelectric Conversion Element Used for Solid-State Image Sensor to which Present Technology is Applied>

Figure 1B:
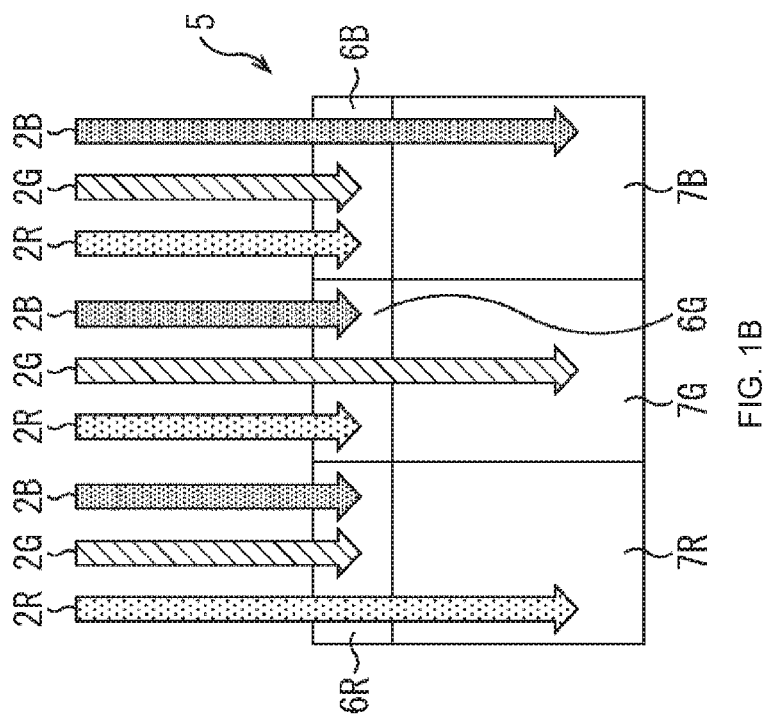
FIGS. 1A and 1B are explanatory diagrams describing a solid-state image sensor FIG. 1A including a photoelectric conversion element of the present technology and a solid-state image sensor FIG. 1B according to a comparative example.
Figure 1A:
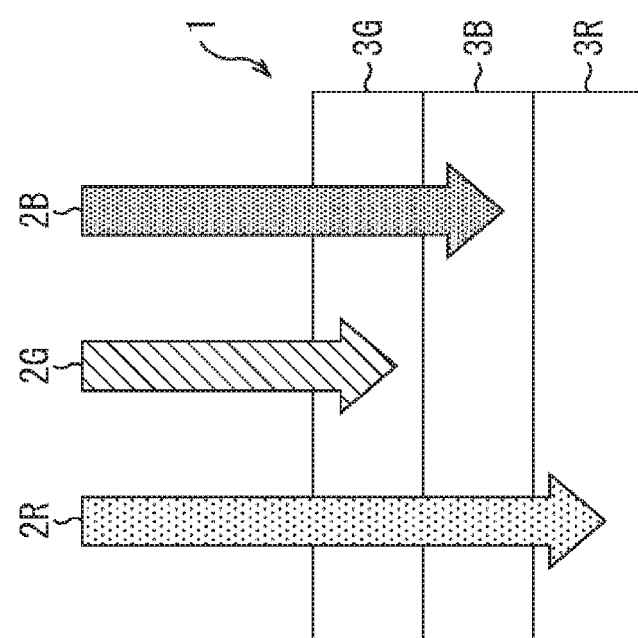

An overview of a photoelectric conversion element of the present technology will now be described with reference to FIGS. 1A and 1B. FIG. 1A is an explanatory diagram describing a solid-state image sensor including a photoelectric conversion element of the present technology, and FIG. 1B is an explanatory diagram describing a solid-state image sensor according to a comparative example.

Hereinafter, in this specification, when it is described that "light of a certain wavelength is absorbed," it means that about 70% or more of light of the wavelength is absorbed. In addition, in contrast, when it is described that "light of a certain wavelength is transmitted" or "light of a certain wavelength is not absorbed," it means that about 70% or more of light of the wavelength is transmitted and about 30% or less of the light is absorbed.

First, a solid-state image sensor according to the comparative example will be described. As illustrated in FIG. 1B, a solid-state image sensor 5 according to the comparative example includes photodiodes 7R, 7G, and 7B and color filters 6R, 6G, and 6B formed on the photodiodes 7R, 7G, and 7B.

The color filters 6R, 6G, and 6B are films that selectively transmit light of a specific wavelength. For example, the color filter 6R selectively transmits the red light 2R having a wavelength of greater than or equal to 600 nm, the color filter 6G selectively transmits the green light 2G having a wavelength of greater than or equal to 450 nm and less than 600 nm, and the color filter 6B selectively transmits the blue light 2B having a wavelength of greater than or equal to 400 nm and less than 450 nm.

The photodiodes 7R, 7G, and 7B are a light detector that absorbs light of a wide wavelength range (for example, the absorption wavelength of a silicon photodiode is 190 nm to 1100 nm). Therefore, it has been difficult for each of the photodiodes 7R, 7G, and 7B alone to extract a signal of a color such as red color, green color, or blue color separately.

Thus, in the solid-state image sensor according to the comparative example, light other than light corresponding to each color is absorbed by the color filter 6R, 6G, or 6B and only light corresponding to each color is selectively transmitted, and thereby color separation is performed; and a signal of each color is extracted by each of the photodiodes 7R, 7G, and 7B.

Hence, in the solid-state image sensor 5 according to the comparative example, most light is absorbed by the color filters 6R, 6G, and 6B, and the photodiodes 7R, 7G, and 7B have been able to utilize substantially only ⅓ of the incident light for photoelectric conversion. Consequently, in the solid-state image sensor 5 according to the comparative example, the improvement in the detection sensitivity of each color has been limited.

Next, a solid-state image sensor 1 including a photoelectric conversion element of the present technology is described. As shown in FIG. 1A, a solid-state image sensor 1 including a photoelectric conversion element of the present technology has a configuration in which a green photoelectric conversion element 3G that absorbs green light 2G, a blue photoelectric conversion element 3B that absorbs blue light 2B, and a red photoelectric conversion element 3R that absorbs red light 2R are stacked in order.

For example, the green photoelectric conversion element 3G is a photoelectric conversion element that selectively absorbs green light with wavelengths of not less than 450 nm and less than 600 nm, the blue photoelectric conversion element 3B is a photoelectric conversion element that selectively absorbs blue light with wavelengths of not less than 400 nm and less than 450 nm, and the red photoelectric conversion element 3R is a photoelectric conversion element that selectively absorbs red light with wavelengths of 600 nm or more.

Therefore, in the solid-state image sensor 1 of the present technology, each of the photoelectric conversion elements can selectively absorb light of a specific wavelength range corresponding to each of red color, green color, and blue color. Hence, in the solid-state image sensor 1 of the present technology, a color filter for separating the incident light into each color is not needed, and all the incident light can be used for photoelectric conversion. Thus, the solid-state image sensor 1 of the present technology can increase the amount of light usable for photoelectric conversion to approximately three times that of the solid-state image sensor 5 according to the comparative example, and can therefore further improve the detection sensitivity of each color.

In addition, in the solid-state image sensor 1 of the present technology, the blue photoelectric conversion element 3B and the red photoelectric conversion element 3R may be a silicon photodiode that photoelectrically converts light of a wide wavelength range (specifically, 190 nm to 1100 nm, or the like). In such a case, the blue photoelectric conversion element 3B and the red photoelectric conversion element 3R separate the colors of blue light 2B and red light 2R using the difference in the entry depth of light into the solid-state image sensor 1 between the wavelengths. Specifically, red light 2R has a longer wavelength than blue light 2B and is less likely to be scattered, and therefore enters up to a depth distant from the incidence surface; on the other hand, blue light 2B has a shorter wavelength than red light 2R and is more likely to be scattered, and therefore enters only to a depth nearer to the incidence surface. Thus, red light 2R can be detected separately from blue light 2R by placing the red photoelectric conversion element 3R in a position distant from the incidence surface of the solid-state image sensor 1. Therefore, even in a case where a silicon photodiode is used for the blue photoelectric conversion element 3B and the red photoelectric conversion element 3R, blue light 2B and red light 2R can be separated using the difference in the entry depth of light, and a signal of each color can be extracted.

Here, each of the photoelectric conversion elements 3G, 3B, and 3R included in the solid-state image sensor 1 of the present technology is required to selectively absorb light of a specific wavelength range corresponding to each of red color, green color, and blue color, and to transmit light of wavelengths other than the absorption wavelengths. In particular, the green photoelectric conversion element 3G, which is nearest to the incidence surface, is required to have an absorption spectrum having a steep peak in the green region (for example, the wavelength range of 450 nm to 600 nm), and to have small absorption in the range of not more than 450 nm and less than 600 nm.

<Configuration of Photoelectric Conversion Element in Solid-State Image Sensor to which Present Technology is Applied>

Figure 2:
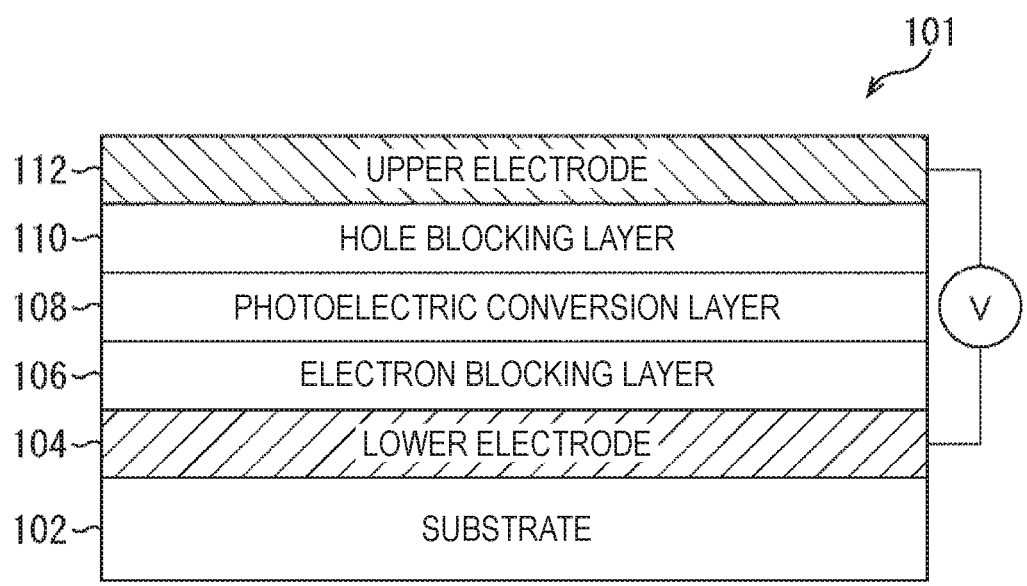
FIG. 2 is a schematic diagram showing the configuration of a photoelectric conversion element according to an embodiment of the present technology.

Next, the configuration of a photoelectric conversion element according to an embodiment of the present technology is described with reference to FIG. 2. FIG. 2 is a schematic diagram showing the configuration of a photoelectric conversion element according to an embodiment of the present technology.

As shown in FIG. 2, a photoelectric conversion element 101 according to a first embodiment of the present technology includes a substrate 102, a lower electrode 104 placed on the substrate 102, an electron blocking layer 106 placed on the lower electrode 104, a photoelectric conversion layer 108 placed on the electron blocking layer 106, a hole blocking layer 110 placed on the photoelectric conversion layer 108, and an upper electrode 112 placed on the hole blocking layer 110.

In addition, the structure of the photoelectric conversion element 101 shown in FIG. 2 is only an example, and the structure of the photoelectric conversion element 101 according to an embodiment of the present technology is not limited to the structure shown in FIG. 2. For example, one or both of the electron blocking layer 106 and the hole blocking layer 110 may be omitted.

The substrate 102 is a support body on which the layers constituting the photoelectric conversion element 101 are arranged to be stacked. As the substrate 102, those used in common photoelectric conversion elements may be used. For example, the substrate 102 may be various glass substrates such as a high strain point glass substrate, a soda glass substrate, and a borosilicate glass substrate, a quartz substrate, a semiconductor substrate, a plastic substrate of polymethyl methacrylate, polyvinyl alcohol, a polyimide, a polycarbonate, or the like, etc. Further, in a case where incident light is allowed to be transmitted through the photoelectric conversion element 101 and the transmitted incident light is received by another photoelectric conversion element, the substrate 102 is preferably configured with a transparent material.

The lower electrode 104 and the upper electrode 112 are configured with an electrically conductive material, and at least one of them is configured with a transparent electrically conductive material. Specifically, the lower electrode 104 and the upper electrode 112 may be formed of indium tin oxide (ITO), indium zinc oxide (IZO), or the like. Further, in a case where incident light is allowed to be transmitted through the photoelectric conversion element 101 and the transmitted incident light is received by another photoelectric conversion element, it is preferable that both of the lower electrode 104 and the upper electrode 112 be configured with a transparent electrically conductive material such as ITO.

Further, a bias voltage is applied to the lower electrode 104 and the upper electrode 112. For example, the bias voltage is applied to set a polarity such that electrons move to the upper electrode 112 and holes move to the lower electrode 104 among charges generated in the photoelectric conversion layer 108.

In addition, it goes without saying that the polarity of the bias voltage may also be set so that, of the charge generated in the photoelectric conversion layer 108, holes move to the upper electrode 112 and electrons move to the lower electrode 104. In such a case, the positions of the electron blocking layer 106 and the hole blocking layer 110 are exchanged in the photoelectric conversion element 101 shown in FIG. 2.

The electron blocking layer 106 suppresses the increase of dark current caused by electrons being injected into the photoelectric conversion layer 108 from the lower electrode 104 when a bias voltage is applied. Specifically, the electron blocking layer 106 is configured with an electron-donating material, and may be configured with, for example, an arylamine, oxazole, an oxadiazole, a triazole, imidazole, a stilbene, a polyarylalkane, a porphyrin, anthracene, fluorenone, or a hydrazone, a derivative of these, or the like. Specifically, the electron blocking layer 106 may be configured with N,N'-bis(3-methylphenyl)-(1,1'-biphenyl)-4,4'-diamine (TPD), 4,4'-bis[N-naphthyl-N-phenylamino]biphenyl (α-NPD), 4,4',4"-tris(N-(3-methylphenyl)-N-phenylamino)triphenyl amine (m-MTDATA), copper tetraphenylporphyrin, phthalocyanine, copper phthalocyanine, or the like.

The photoelectric conversion layer 108 selectively absorbs light of specific wavelengths, and photoelectrically converts the absorbed light. Specifically, the photoelectric conversion layer 108 is configured with a photoelectric conversion film made of only a compound represented by Chemical Formula (1) below.

[Chem. 1]

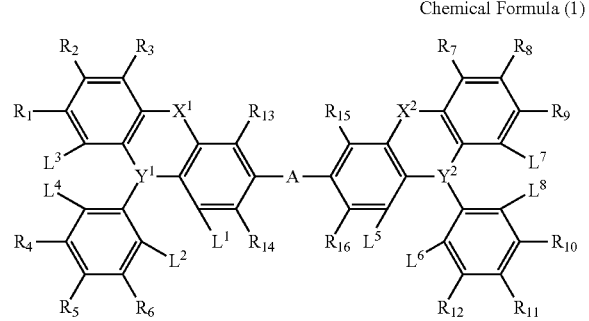

Chemical Formula (1)

A in Chemical Formula (1) may be a compound having a structure expressed by any of Chemical Formula (2) to Chemical Formula (8) below; but it is preferable that A in Chemical Formula (1) be an aryl group or a heteroaryl group and have a molecular weight of 75 or more; further, it is preferable that the molecular weight of the compound represented by Chemical Formula (1) be not less than 620 and not more than 1000 as a whole. In addition, B of Chemical Formula (3) is different from A in Chemical Formula (1), and each represents a carbon atom or a nitrogen atom. Further, R21 of Chemical Formula (6) is an aryl group or a heteroaryl group.

[Chem. 2]

Chemical Formula (2)

[Chem. 3]

Chemical Formula (3)

[Chem. 4]

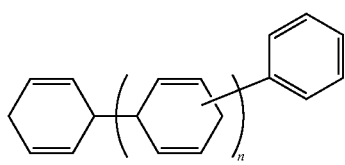

Chemical Formula (4)

[Chem. 5]

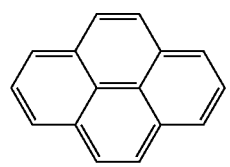

Chemical Formula (5)

[Chem. 6]

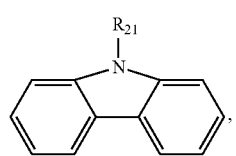

Chemical Formula (6)

[Chem. 7]

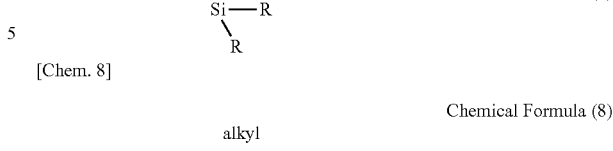

Chemical Formula (7)

[Chem. 8]

Chemical Formula (8)

alkyl

Further, Y1 and Y2 in Chemical Formula (1) represent a linker that links via one atom selected from the group consisting of a nitrogen atom, a boron atom, and a phosphorus atom.

Furthermore, X1 and X2 in Chemical Formula (1) represent a linker that links via one atom selected from the group consisting of an oxygen atom, a sulfur atom, a carbon atom, a nitrogen atom, a phosphorus atom, and a silicon atom.

Further, one of a set of L1 and L2 and a set of L3 and L4 in Chemical Formula (1) represent a linker that, by binding to each other, links via one atom selected from the group consisting of an oxygen atom, a sulfur atom, a carbon atom, a nitrogen atom, a phosphorus atom, and a silicon atom.

Furthermore, one of a set of L5 and L6 and a set of L7 and L8 in Chemical Formula (1) represent a linker that, by binding to each other, links via one atom selected from the group consisting of an oxygen atom, a sulfur atom, a carbon atom, a nitrogen atom, a phosphorus atom, and a silicon atom.

Further, each of R1 to R16 in Chemical Formula (1) represents an independent hydrogen atom or a linker that links via one atom selected from the group consisting of substituents other than a hydrogen atom.

Therefore, the photoelectric conversion layer 108 can selectively absorb green light (for example, light of wavelengths of not less than 450 nm and less than 600 nm). In addition, it is more preferable that A and R1 to R16 in Chemical Formula (1) have no alkyl group. Further, in the compound of Chemical Formula (4), n is preferably n=1 to 5.

Furthermore, Chemical Formula (1) may be expressed by, for example, Chemical Formula (9) below, depending on the structure of A.

[Chem. 9]

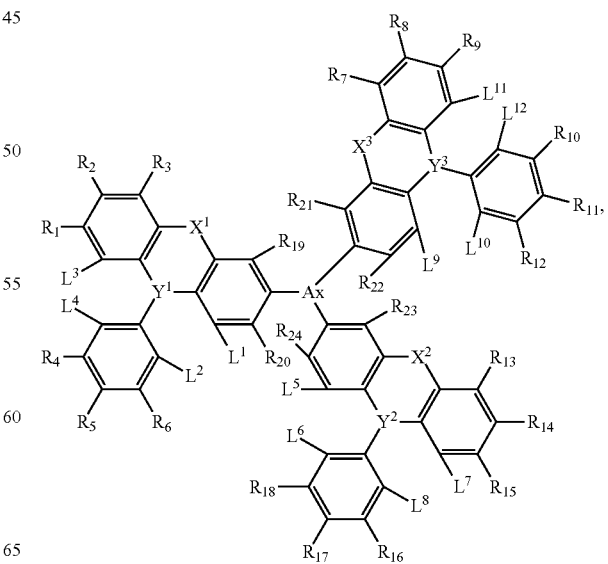

Chemical Formula (9)

Here, Ax may be similar to Chemical Formula (3) described above, for example.

Further, in Chemical Formula (9), each of R1 to R24 represents an independent hydrogen atom or a linker that links via one atom selected from the group consisting of a carbon atom.

The hole blocking layer 110 suppresses the increase of dark current caused by holes being injected into the photoelectric conversion layer 108 from the upper electrode 112 when a bias voltage is applied. Specifically, the hole blocking layer 110 is configured with an electron-accepting material, and may be configured with, for example, fullerenes, carbon nanotubes, an oxadiazole, a triazole compound, an anthraquinodimethane, a diphenylquinone, a distyrylarylene, or a silole compound, a derivative of these, or the like. Specifically, the hole blocking layer 110 may be configured with 1,3-bis(4-tert-butylphenyl-1,3,4-oxadiazolyl)phenylene (OCD-7), bathocuproine, bathophenanthroline, aluminum tris(8-hydroxyquinolinate) (Alq3), or the like.

In addition, in the structure of the photoelectric conversion element 101 illustrated in FIG. 2, materials forming layers other than the photoelectric conversion layer 108 are not specifically limited, but a known material for the photoelectric conversion element may also be used.

Here, each of the layers in the photoelectric conversion element 101 according to an embodiment of the present technology described above may be formed by an appropriate film formation method that is selected according to a material such as a vacuum deposition, a sputtering, and various coating methods.

For example, in each of the layers forming the photoelectric conversion element 101 according to an embodiment of the present technology, the lower electrode 104 and the upper electrode 112 may be formed by a deposition method including an electron beam deposition method, a hot filament deposition method and a vacuum deposition method, a sputtering method, a combination of a chemical vapor deposition method (CVD method), an ion plating method and an etching method, various types of printing methods such as a screen printing method, an ink jet printing method and a metal mask printing method, or a plating method (an electroplating method and an electroless plating method), and the like.

Further, among the layers constituting the photoelectric conversion element 101 according to an embodiment of the present technology, the electron blocking layer 106, the photoelectric conversion layer 108, the hole blocking layer 110, etc. may be formed by, for example, deposition methods such as the vacuum deposition method, printing methods such as the screen printing method and the ink jet printing method, the laser transfer method, coating methods such as the spin coating method, etc.

<Specific Examples of Photoelectric Conversion Film Configuring Photoelectric Conversion Layer>

The photoelectric conversion layer 108 of the photoelectric conversion element 101 in a solid-state image sensor to which the present technology is applied is configured with any of the compounds of Chemical Formula (1) described above. Among them, for example, Compounds 1 to 9 shown by FIG. 3 will now be described. These Compounds 1 to 9 are compounds represented by Chemical Formula (10) to Chemical Formula (18) below.

[Chem. 10]

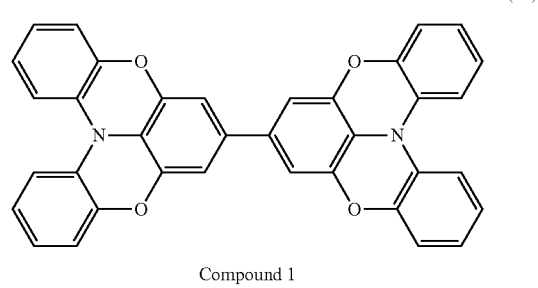

Chemical Formula (10)

Compound 1

[Chem. 11]

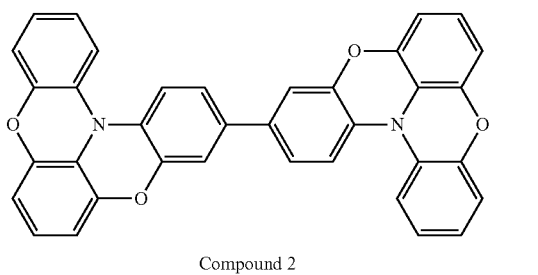

Chemical Formula (11)

Compound 2

[Chem. 12]

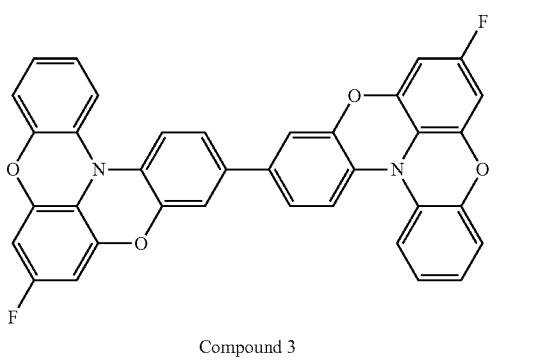

Chemical Formula (12)

Compound 3

[Chem. 13]

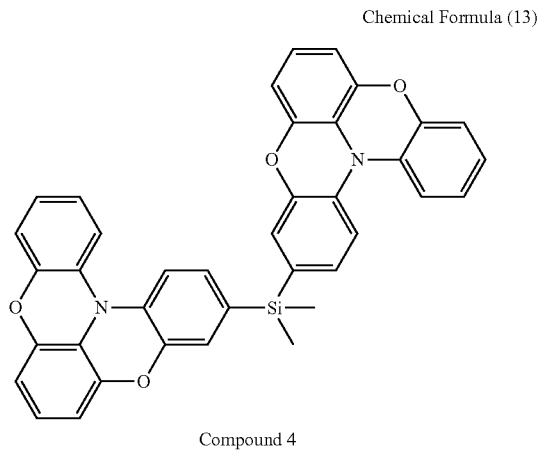

Chemical Formula (13)

Compound 4

[Chem. 14]

Chemical Formula (14)

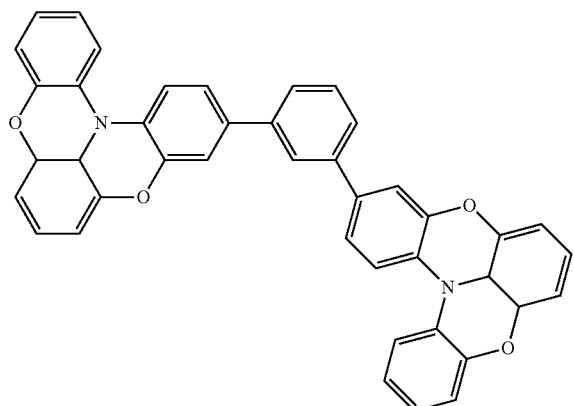

Compound 5

[Chem. 15]

Chemical Formula (15)

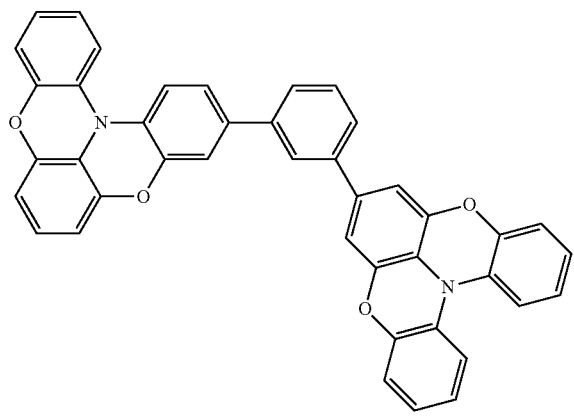

Compound 6

[Chem. 16]

Chemical Formula (16)

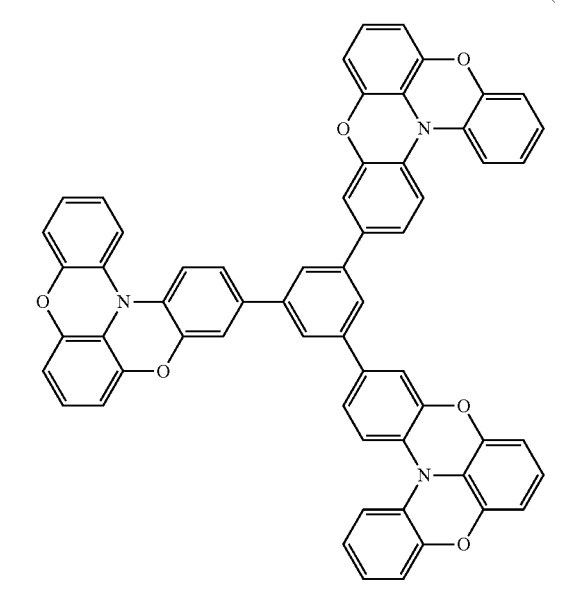

Compound 7

[Chem. 17]

Chemical Formula (17)

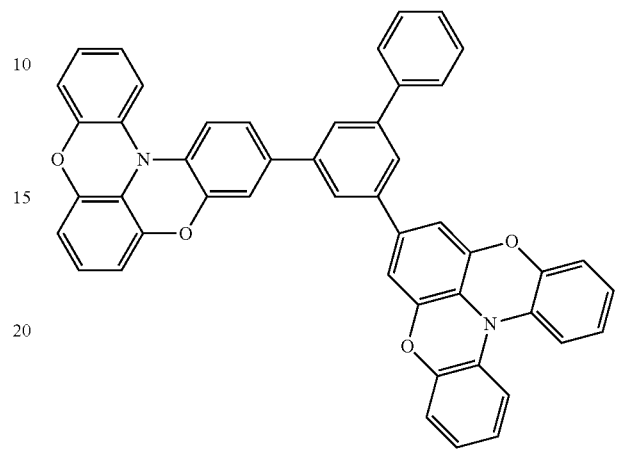

Compound 8

[Chem. 18]

Chemical Formula (18)

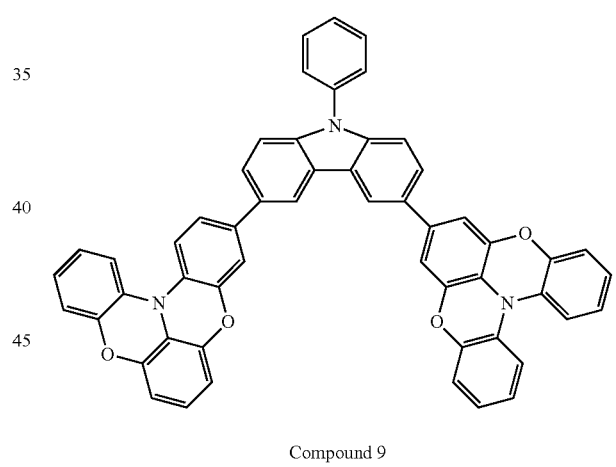

Compound 9

In Compound 1 of FIG. 3, the absorption peak wavelength (λmax) is 374 nm, cohesion due to annealing at high temperature is observed (optical microscopic observation; the observation of the surface with an optical microscope), and the photoelectric conversion efficiency (EQE) is made 12% by being formed as a bulk hetero-layer (p-type:n-type=1:1, N=Compound X), but there is a tendency for the spectral shape to spread a little (spectral shape: broad).

Here, Compound X is a subphthalocyanine chloride, and is the compound represented by Chemical Formula (19) below.

[Chem. 19]

Chemical Formula (19)

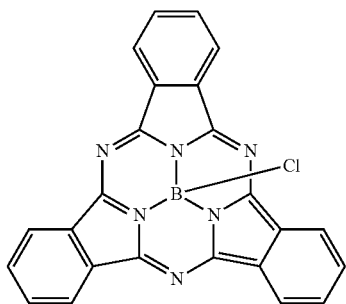

In Compound 2 of FIG. 3, the absorption peak wavelength (λmax) is 407 nm, cohesion due to annealing at high temperature is observed (optical microscopic observation), and the photoelectric conversion efficiency (EQE) is slightly improved by being formed as a bulk hetero-layer (p-type: n-type=1:1, N=Compound X).

In Compound 3 of FIG. 3, the absorption peak wavelength (λmax) is 409 nm, cohesion due to annealing at high temperature is observed (optical microscopic observation), and the photoelectric conversion efficiency (EQE) is slightly improved by being formed as a bulk hetero-layer (p-type: n-type=1:1, N=Compound X).

In Compound 4 of FIG. 3, the absorption peak wavelength (λmax) is 372 nm, cohesion due to annealing at high temperature is observed (optical microscopic observation), and the photoelectric conversion efficiency (EQE) is slightly improved by being formed as a bulk hetero-layer (p-type: n-type=1:1, N=Compound X).

In Compound 5 of FIG. 3, the absorption peak wavelength (λmax) is 388 nm, cohesion due to annealing at high temperature does not occur (optical microscopic observation), and the photoelectric conversion efficiency (EQE) is made 7% by being formed as a bulk hetero-layer (p-type: n-type=1:1, N=Compound X).

In Compound 6 of FIG. 3, the absorption peak wavelength (λmax) is 382 nm, cohesion due to annealing at high temperature does not occur (optical microscopic observation), and the photoelectric conversion efficiency (EQE) is slightly improved by being formed as a bulk hetero-layer (p-type:n-type=1:1, N=Compound X).

In Compound 7 of FIG. 3, the absorption peak wavelength (λmax) is 394 nm, cohesion due to annealing at high temperature does not occur (optical microscopic observation), and the photoelectric conversion efficiency (EQE) is slightly improved by being formed as a bulk hetero-layer (p-type:n-type=1:1, N=Compound X).

In Compound 8 of FIG. 3, the absorption peak wavelength (λmax) is 385 nm, cohesion due to annealing at high temperature does not occur (optical microscopic observation), and the photoelectric conversion efficiency (EQE) is slightly improved by being formed as a bulk hetero-layer (p-type:n-type=1:1, N=Compound X).

In Compound 9 of FIG. 3, the absorption peak wavelength (λmax) is 380 nm, cohesion due to annealing at high temperature does not occur (optical microscopic observation), and the photoelectric conversion efficiency (EQE) is slightly improved by being formed as a bulk hetero-layer (p-type:n-type=1:1, N=Compound X).

That is, in all of Compounds 1 to 9, as a photoelectric conversion film configuring the photoelectric conversion layer 108, the photoelectric conversion efficiency (EQE) is improved as compared to a photoelectric conversion layer configured with only Compound X, by being formed as a bulk hetero-layer. The EQE, which is 3% in a case where a photoelectric conversion layer configured with only Compound X is used, is made 12% by using Compound 1, and is made 7% by using Compound 5. However, for Compound 1, the spectral shape spreads (spectral shape: broad). Further, in all of Compounds 1 to 4, cohesion due to annealing at high temperature is seen, and therefore the heat resistance is poor.

However, for Compound 5, cohesion due to annealing at high temperature is not seen, and further the photoelectric conversion efficiency (EQE) is made 7%; therefore, Compound 5 can be said to be most suitable among the seven kinds of compounds in FIG. 3 in terms of spectral characteristics, photoelectric conversion characteristics, and heat resistance, as the material of a photoelectric conversion film configuring the photoelectric conversion layer 108.

Figure 4:
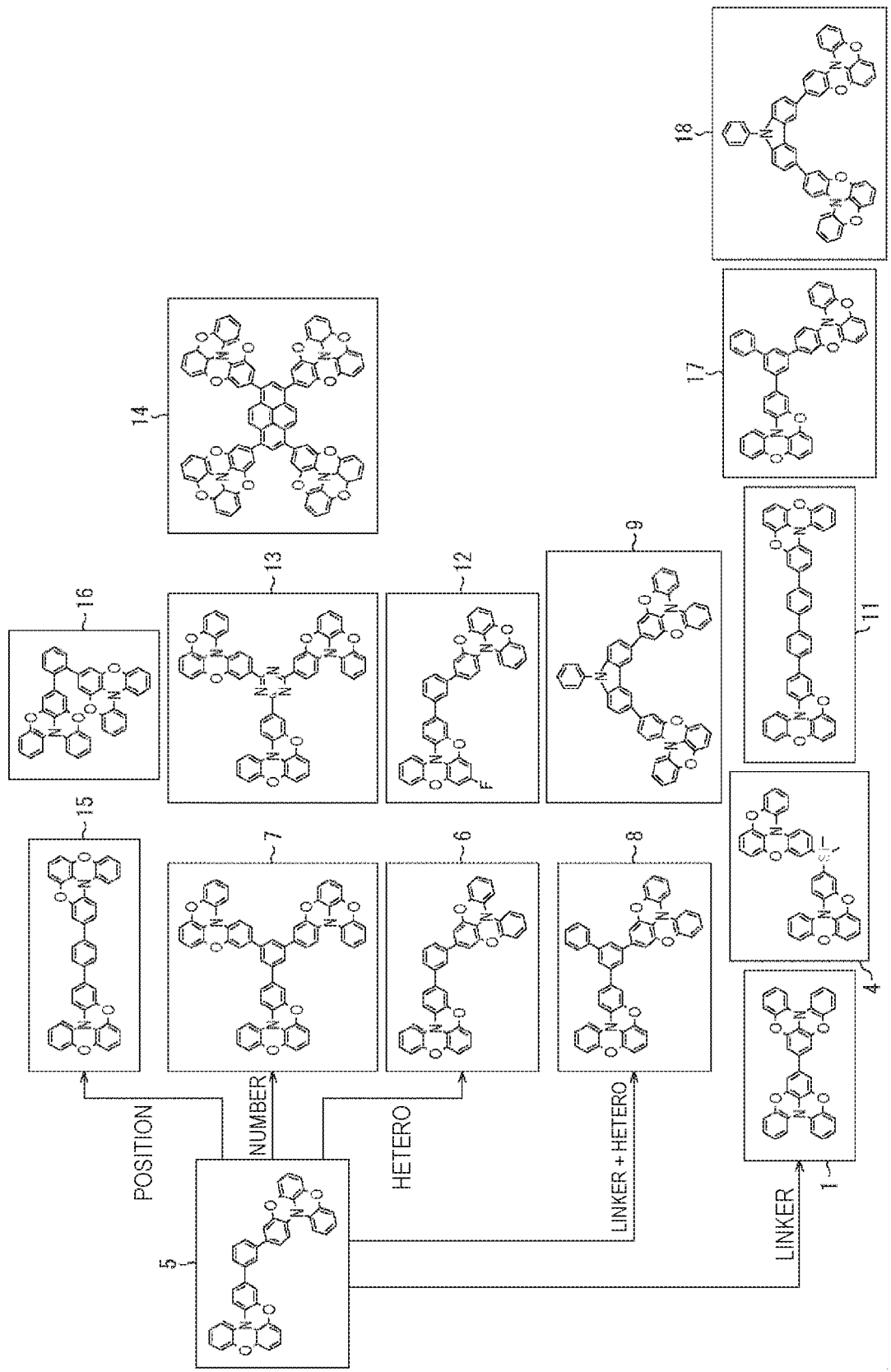
FIG. 4 is a diagram describing specific examples of the compound.

In addition, as a photoelectric conversion film configuring the photoelectric conversion layer 108, any compound corresponding to Chemical Formula (1) described above improves the photoelectric conversion efficiency by being formed as a bulk hetero-layer; specifically, in addition to Compounds 1 to 9 of FIG. 3, Compounds 11 to 18 shown by FIG. 4 and the like are possible, for example. In addition, Compounds 11 to 18 are the compounds expressed by Chemical Formula (20) to Chemical Formula (27) below, respectively.

[Chem. 20]

Chemical Formula (20)

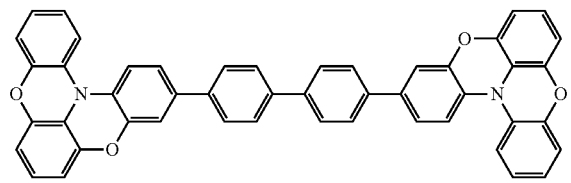

Compound 11

[Chem. 21]

Chemical Formula (21)

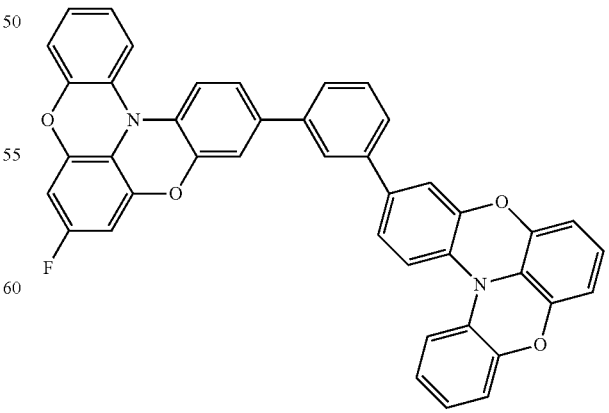

Compound 12

[Chem. 22]
Chemical Formula (22)
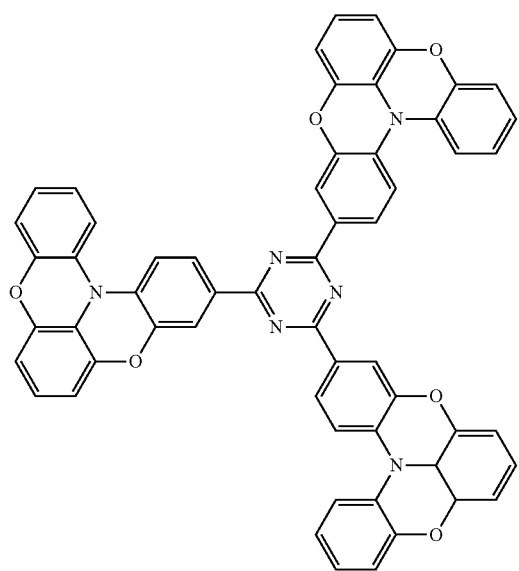
Compound 13
[Chem. 23]
Chemical Formula (23)
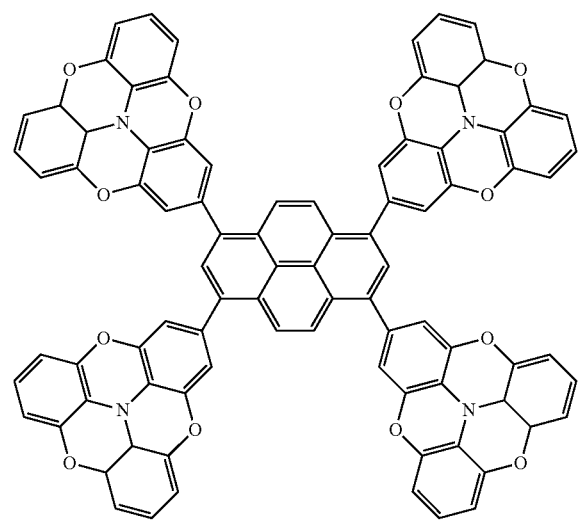
Compound 14
[Chem. 24]
Chemical Formula (24)
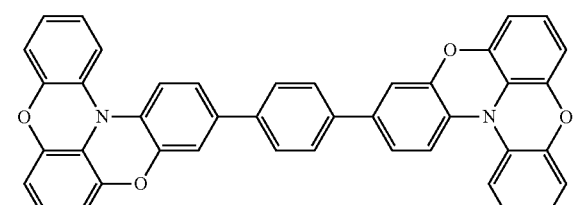
Compound 15
[Chem. 25]
Chemical Formula (25)
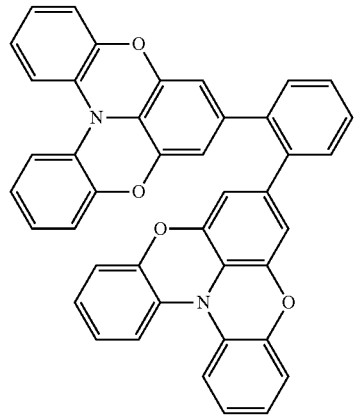
Compound 16
[Chem. 26]
Chemical Formula (26)
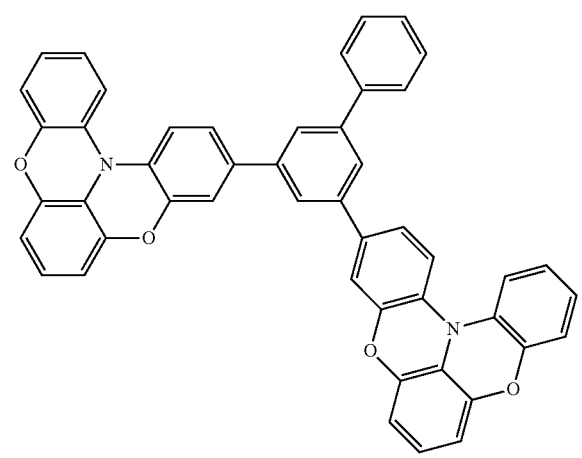
Compound 17
[Chem. 27]
Chemical Formula (27)
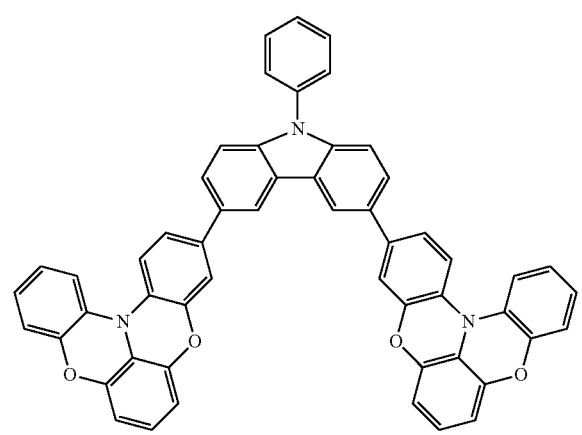
Compound 18

As shown by FIG. 4, Compounds 1, 4, 11, 17, and 18 are a linker of Compound 5 that is most suitable, Compounds 6 and 12 are a hetero of Compound 5, and Compounds 8 and 9 are a linker+a hetero of Compound 5. Further, Compounds 7, 13, and 14 are compounds in which the number of side chains connected to A of Compound 5 is different, and Compounds 15 and 16 are examples in which the arrangement connected to A of Compound 5 is different.

Further, among the compounds represented by Chemical Formula (1), a compound that coheres is a case where there is no linker or the linker is not an aryl group or a heteroaryl group, and furthermore has a molecular weight of the compound represented by Chemical Formula (1) of approximately 620 or less. That is, in a case where there is a linker and the linker is an aryl group or a heteroaryl group, the film quality is not changed by annealing. Hence, the molecular weight of the compound represented by Chemical Formula (1) is preferably larger than approximately 620.

Further, in the compound represented by Chemical Formula (1), if heating is not performed carefully, material decomposition of the oxygen-crosslinked triarylamine part occurs during film formation based on deposition. In general, in view of the fact that the heat load during deposition increases as the molecular weight increases, a compound in which the molecular weight is more than 1000 and the linker is an aryl group or a heteroaryl group is accompanied by material decomposition during film formation based on deposition. Therefore, the molecular weight of the compound represented by Chemical Formula (1) is preferably smaller than 1000.

<Use for Electron Blocking Layer>

In the above, an example in which a compound of Chemical Formula (1) described above is used as a photoelectric conversion film of the photoelectric conversion layer 108 is described; but it has been found that a compound of Chemical Formula (1) has heat resistance while keeping transparency and furthermore reduces dark current.

Thus, a compound of Chemical Formula (1) may be used for a buffer layer configuring the electron blocking layer 106.

Therefore, a compound of Chemical Formula (1) can be used for both of the electron blocking layer 106 and the photoelectric conversion layer 108; and can reduce dark current while keeping transparency by being used as the electron blocking layer 106, and can improve spectral characteristics and photoelectric conversion characteristics by being used as the photoelectric conversion layer 108.

{Use for Green Photoelectric Conversion Film}

Furthermore, in a case where a compound of Chemical Formula (1) is used for the electron blocking layer 106, a high effect can be obtained by use as a green photoelectric conversion film. In the following, reasons why a high effect is obtained by use as a green photoelectric conversion film in a case where a compound of Chemical Formula (1) is used for the electron blocking layer 106 are described.

{1. Level}

In a photoelectric conversion film that absorbs green light, in general, a P-type semiconductor material having an energy level in the range of 5.3 to 5.8 eV is used in many cases in order to transport holes.

On the other hand, a transparent electrode that is formed above and below the green photoelectric conversion element and that is fabricated using a transparent electrically conductive material generally has a work function in the range of 4.5 to 5.2 eV in many cases.

The electron blocking layer 106 described with reference to FIG. 2 contains a compound represented by Chemical Formula (1), and the electron blocking layer 106 has an energy level in the range of 5.2 to 5.7 eV.

Therefore, by using the present technology, it becomes possible to provide an electron blocking layer 106 having a value between the energy level of the green photoelectric conversion film and the work function of the transparent electrode or a value equal to one of them.

This means that, by using the present technology, the charge transportation of carriers generated in the green photoelectric conversion film to the transparent electrode can be performed smoothly.

Thus, the use of the present technology as an electron blocking layer for a green photoelectric conversion film is expected to provide an effect in which, while the effect of reducing dark current by the introduction of an electron blocking layer, which is generally said, is exhibited, important characteristics in a solid-state image sensor such as the photoelectric conversion efficiency (EQE) and the optical responsiveness are not impaired.

Hence, when fabricating a solid-state image sensor using a green photoelectric conversion film, it is effective to provide the electron blocking layer 106 using the present technology.

{2. Mobility}

In a photoelectric conversion film that absorbs green light, in general, a hole mobility in the range of $1 \times 10^{-3}$ to $1 \times 10^{-6}$ $cm^2/Vs$ is provided in many cases in order to transport holes.

The electron blocking layer 106 described with reference to FIG. 2 contains a compound represented by Chemical Formula (1), and the hole mobility thereof is in the range of $1 \times 10^{-2}$ to $1 \times 10^{-5}$ $cm^2/Vs$.

Hence, by using the present technology, an electron blocking layer can be provided such that the hole mobility of the green photoelectric conversion film and the hole mobility of the electron blocking layer 106 are equal or the electron blocking layer 106 has a faster hole mobility.

This means that, by using the present technology, the charge transportation of carriers generated in the green photoelectric conversion film to the transparent electrode can be performed smoothly via the electron blocking layer.

Thus, the use of the present technology as an electron blocking layer for a green photoelectric conversion film is expected to provide an effect in which, while the effect of reducing dark current by the introduction of an electron blocking layer, which is generally said, is exhibited, important characteristics in a solid-state image sensor such as the photoelectric conversion efficiency (EQE) and the optical responsiveness are not impaired.

Hence, when fabricating a solid-state image sensor using a green electric conversion film, it is effective to provide an electron blocking layer using the present technology.

{3. Oxygen}

In a solid-state image sensor using a photoelectric conversion film that absorbs green light, a transparent electrode is formed above and below the green photoelectric conversion film.

The transparent electrode is an inorganic oxide such as ITO or IZO in many cases.

The electron blocking layer 106 described with reference to FIG. 2 contains any of the compounds represented by Chemical Formula (1), and these contain an oxygen atom in their framework.

This oxygen atom is expected to interact with a transition metal exposed on the outermost surface of the inorganic oxide of the transparent electrode to form a good contact with the electrode.

This oxygen atom is expected to replace an oxygen atom exposed on the outermost surface of the inorganic oxide of the transparent electrode to form a good contact with the electrode.

Thus, by the formation of a good contact with the electrode, it is expected that the transportation of holes between the electrode and the electron blocking layer is performed smoothly.

Thus, the use of the present technology as an electron blocking layer for a green photoelectric conversion film is expected to provide an effect in which, while the effect of reducing dark current by the introduction of an electron blocking layer, which is generally said, is exhibited, important characteristics in a solid-state image sensor such as the photoelectric conversion efficiency (EQE) and the optical responsiveness are not impaired.

Hence, when fabricating a solid-state image sensor using a green electric conversion film, it is effective to provide an electron blocking layer using the present technology.

{4. Anisotropy}

In a solid-state image sensor using a photoelectric conversion film that absorbs green light, it is necessary to consider the carrier mobility in directions perpendicular and horizontal to the light receiving surface of the formed organic photoelectric conversion film.

In general, it is preferable that the carrier mobility in a horizontal direction be higher than the carrier mobility in a direction perpendicular to the light receiving surface.

Thereby, carriers generated in the green photoelectric conversion film in a pixel can be prevented from being read in another pixel in the neighborhood.

The electron blocking layer 106 described with reference to FIG. 2 contains any of the compounds represented by Chemical Formula (1), and in these it is expected that the carrier mobility in a direction horizontal to the light receiving surface is higher than the carrier mobility in a direction perpendicular to the light receiving surface.

One cause of this is the property possessed by the electron blocking layer 106 of FIG. 2 that it is easy to obtain horizontal orientation with respect to the substrate.

Thus, by using the present technology as an electron blocking layer for a green photoelectric conversion film, a solid-state image sensor with smaller interference between pixels, in other words, a more excellent solid-state image sensor can be fabricated.

<Configuration of Solid-State Image Sensor>

Figure 5A:
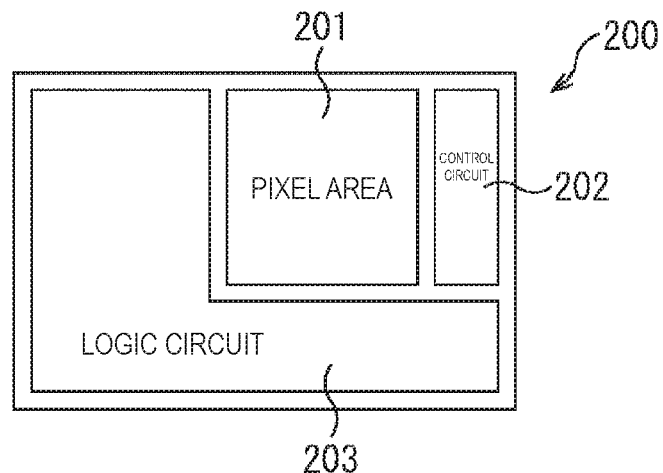
FIGS. 5A, 5B and 5C are schematic diagrams showing the structure of a solid-state image sensor in which a photoelectric conversion element of the present technology is used.
Figure 5B:
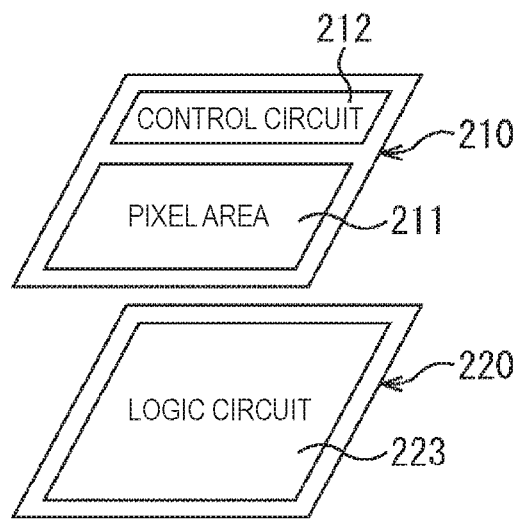
Figure 5C:
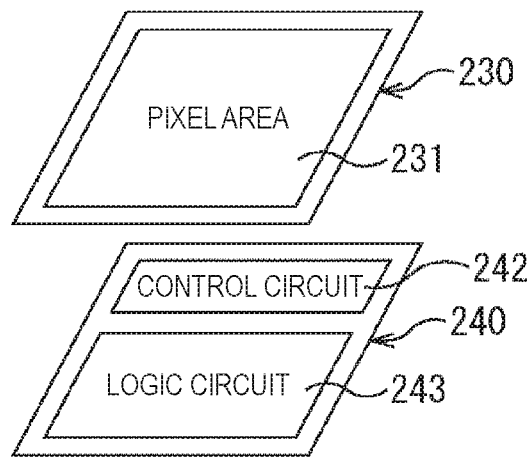

Next, a configuration of the solid-state image sensor to which the photoelectric conversion element according to the present technology is applied will be described with reference to FIGS. 5A, 5B, 5C and 6. FIGS. 5A, 5B and 5C are schematic diagrams illustrating a structure of a solid-state image sensor to which the photoelectric conversion element according to the present technology is applied.

Here, in FIGS. 5A, 5B and 5C, pixel areas 201, 211 and 231 are areas in which the photoelectric conversion element including the photoelectric conversion film according to the present technology are disposed. In addition, control circuits 202, 212 and 242 are arithmetic processing circuits configured to control each component of the solid-state image sensor. Logic circuits 203, 223 and 243 are signal processing circuits configured to process a signal obtained by photoelectric conversion of the photoelectric conversion element in the pixel area.

For example, as illustrated in a component FIG. 5A, in the solid-state image sensor to which the photoelectric conversion element according to the present technology is applied, the pixel area 201, the control circuit 202 and the logic circuit 203 may be formed in one semiconductor chip 200.

In addition, as illustrated in a component FIG. 5B, the solid-state image sensor to which the photoelectric conversion element according to the present technology is applied may be a laminated type solid-state image sensor in which the pixel area 211 and the control circuit 212 are formed in a first semiconductor chip 210, and the logic circuit 223 is formed in a second semiconductor chip 220.

Further, as illustrated in a component FIG. 5C, the solid-state image sensor to which the photoelectric conversion element according to the present technology is applied may be a laminated type solid-state image sensor in which the pixel area 231 is formed in a first semiconductor chip 230 and the control circuit 242 and the logic circuit 243 are formed in a second semiconductor chip 240.

In the solid-state image sensors illustrated in the components FIGS. 5B and 5C, at least one of the control circuit and the logic circuit is formed in a semiconductor chip different from the semiconductor chip in which the pixel area is formed. Accordingly, since the solid-state image sensors illustrated in the components FIGS. 5B and 5C can extend the pixel area more than the solid-state image sensor illustrated in the component FIG. 5A, the number of pixels accommodated in the pixel area is increased. Therefore, it is possible to increase a plane resolution. For this reason, it is more preferable that the solid-state image sensor to which the photoelectric conversion element according to the present technology is applied be the laminated type solid-state image sensor illustrated in the components FIGS. 5B and 5C.

Figure 6:
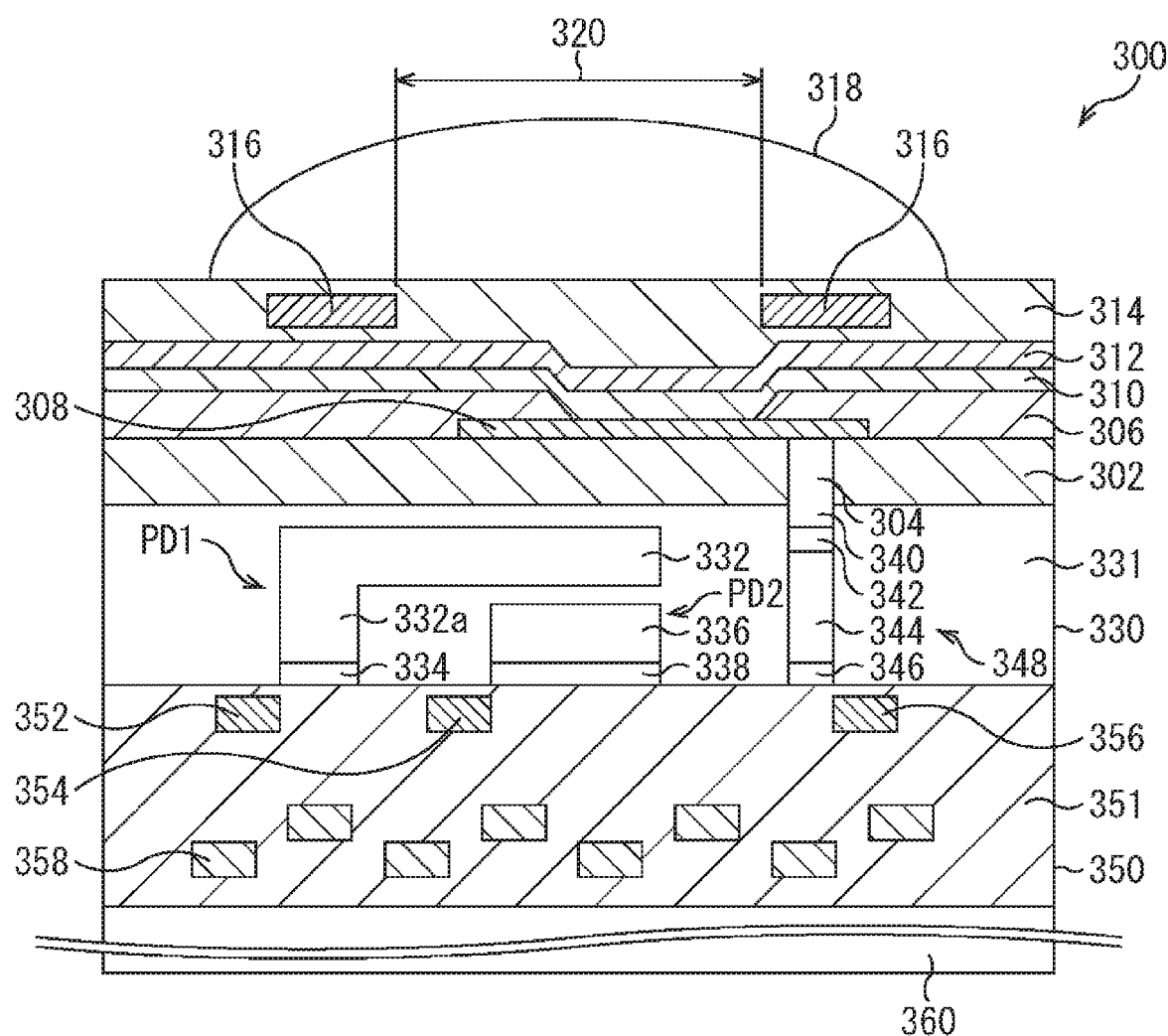

Subsequently, a specific structure of a solid-state image sensor to which the photoelectric conversion element according to the present technology is applied will be described with reference to FIG. 6. FIG. 6 is a cross sectional view illustrating an outline structure of a unit pixel of a solid-state image sensor to which the photoelectric conversion element according to the present technology is applied. In addition, a solid-state image sensor 300 illustrated in FIG. 6 is a rear surface irradiation type solid-state image sensor in which light is incident from a surface opposite to a surface in which a pixel transistor and the like are formed. In addition, in FIG. 6, with respect to the drawing, an upper side is a light receiving surface, and a lower side is a circuit forming surface in which the pixel transistor and a peripheral circuit are formed.

As illustrated in FIG. 6, the solid-state image sensor 300 has a configuration in which, in a photoelectric conversion area 320, a photoelectric conversion element including a first photodiode PD1 formed in a semiconductor substrate 330, a photoelectric conversion element including a second photodiode PD2 formed in the semiconductor substrate 330 and a photoelectric conversion element including an organic photoelectric conversion film 310 formed at a rear surface side of the semiconductor substrate 330 are laminated in a direction of incidence of light.

The first photodiode PD1 and the second photodiode PD2 are formed in a well area 331 that is a first conductivity type (for example, a p type) semiconductor area of the semiconductor substrate 330 made of silicon.

The first photodiode PD1 includes an n type semiconductor area 332 according to a second conductivity type (for example, an n type) impurity formed at a light receiving surface side of the semiconductor substrate 330 and an extending portion 332a that is formed by extending a part thereof to reach a surface side of the semiconductor substrate 330. A high concentration p type semiconductor area 334 serving as a charge accumulation layer is formed on a surface of the extending portion 332a. In addition, the extending portion 332a is formed as an extraction layer for extracting a signal charge accumulated in the n type semiconductor area 332 of the first photodiode PD1 to a surface side of the semiconductor substrate 330.

The second photodiode PD2 includes an n type semiconductor area 336 formed at a light receiving surface side of the semiconductor substrate 330 and a high concentration p type semiconductor area 338 that is formed at a surface side of the semiconductor substrate 330 to become a charge accumulation layer.

In the first photodiode PD1 and the second photodiode PD2, when the p type semiconductor area is formed at an interface of the semiconductor substrate 330, it is possible to suppress the dark current generated at the interface of the semiconductor substrate 330.

Here, the second photodiode PD2 formed in an area that is farthest from the light receiving surface is, for example, a red photoelectric conversion element that absorbs red light and performs photoelectric conversion. In addition, the first photodiode PD1 formed closer to the light receiving surface side than the second photodiode PD2 is, for example, a blue photoelectric conversion element that absorbs blue light and performs photoelectric conversion.

The organic photoelectric conversion film 310 is formed on a rear surface of the semiconductor substrate 330 through an antireflection film 302 and an insulation film 306. In addition, the organic photoelectric conversion film 310 is interposed between an upper electrode 312 and a lower electrode 308 to form the photoelectric conversion element. Here, the organic photoelectric conversion film 310 is, for example, an organic film that absorbs green light and performs photoelectric conversion and is formed as the photoelectric conversion film according to the present technology described above. In addition, the upper electrode 312 and the lower electrode 308 are made of, for example, a transparent conductive material such as indium tin oxide (ITO) or indium zinc oxide (IZO).

In addition, the lower electrode 308 is connected to a vertical transfer path 348 that is formed from the rear surface side to the surface side of the semiconductor substrate 330 through a contact plug 304 penetrating the antireflection film 302. The vertical transfer path 348 is formed to have a structure in which a connecting portion 340, a potential barrier layer 342, a charge accumulation layer 344 and a p type semiconductor area 346 are laminated from the rear surface side of the semiconductor substrate 330.

The connecting portion 340 includes an n type impurity area of a high impurity concentration that is formed at the rear surface side of the semiconductor substrate 330 and is formed for an ohmic contact with the contact plug 304. The potential barrier layer 342 includes a p type impurity area of a low concentration and forms a potential barrier between the connecting portion 340 and the charge accumulation layer 344. The charge accumulation layer 344 accumulates a signal charge transmitted from the organic photoelectric conversion film 310 and is formed in an n type impurity area of a lower concentration than the connecting portion 340. In addition, the p type semiconductor area 346 of a high concentration is formed on a surface of the semiconductor substrate 330. With this p type semiconductor area 346, it is possible to suppress the dark current generated at the interface of the semiconductor substrate 330.

Here, at the surface side of the semiconductor substrate 330, a multilayer wiring layer 350 including wires 358 laminated in a plurality of layers is formed through an interlayer insulating layer 351. In addition, in the vicinity of the surface of the semiconductor substrate 330, read circuits 352, 354 and 356 corresponding to the first photodiode PD1, the second photodiode PD2 and the organic photoelectric conversion film 310 are formed. The read circuits 352, 354 and 356 read a signal output from each photoelectric conversion element and transmit the signal to the logic circuit (not illustrated). Further, a supporting substrate 360 is formed on a surface of the multilayer wiring layer 350.

On the other hand, at a light receiving surface side of the upper electrode 312, a light shielding film 316 is formed to shield the extending portion 332a of the first photodiode PD1 and the vertical transfer path 348. Here, a separate area between the light shielding films 316 is the photoelectric conversion area 320. In addition, an on-chip lens 318 is formed above the light shielding film 316 through a flattening film 314.

The solid-state image sensor 300 to which the photoelectric conversion element according to the present technology is applied has been described above. In addition, in the solid-state image sensor 300 to which the photoelectric conversion element according to the present technology is applied, since color separation is performed on a unit pixel in a longitudinal direction, a color filter and the like are not provided.

<Configuration of Electronic Device>

Figure 7:
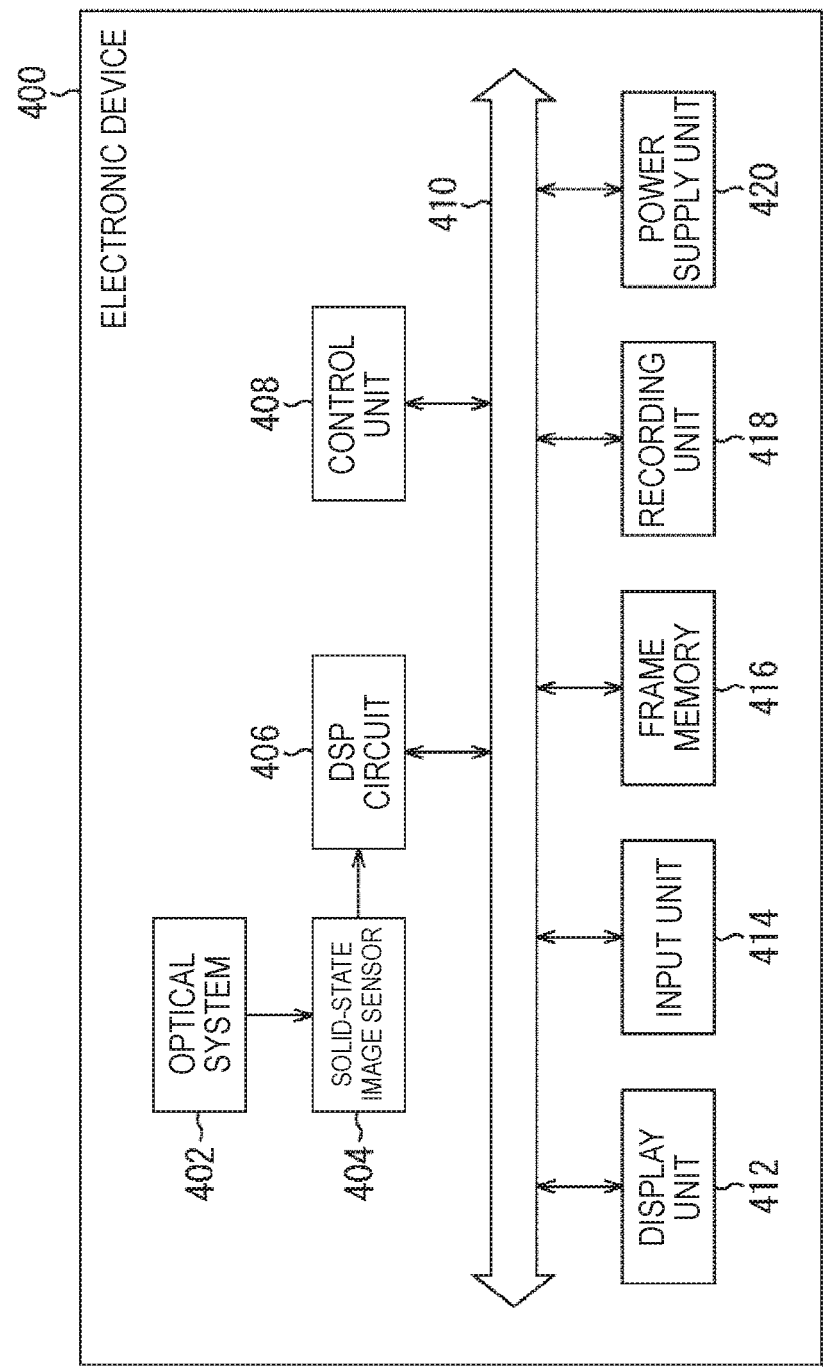

Next, a configuration of an electronic device to which the photoelectric conversion element according to the present technology is applied will be described with reference to FIG. 7. FIG. 7 is a block diagram illustrating a configuration of an electronic device to which the photoelectric conversion element according to the present technology is applied.

As illustrated in FIG. 7, an electronic device 400 includes an optical system 402, a solid-state image sensor 404, a digital signal processor (DSP) circuit 406, a control unit 408, an output unit 412, an input unit 414, a frame memory 416, a recording unit 418 and a power supply unit 420.

Here, the DSP circuit 406, the control unit 408, the output unit 412, the input unit 414, the frame memory 416, the recording unit 418 and the power supply unit 420 are connected to each other via a bus line 410.

The optical system 402 obtains incident light from an object and forms an image on an imaging surface of the solid-state image sensor 404. In addition, the solid-state image sensor 404 includes the photoelectric conversion element according to the present technology, converts an intensity of incident light focused on an imaging surface by the optical system 402 into an electrical signal in units of pixels, and outputs the result as a pixel signal.

The DSP circuit 406 processes the pixel signal transmitted from the solid-state image sensor 404 and outputs the result to the output unit 412, the frame memory 416, the recording unit 418 and the like. In addition, the control unit 408 includes, for example, an arithmetic processing circuit, and controls operations of each of the components of the electronic device 400.

The output unit 412 is, for example, a panel type display device such as a liquid crystal display and an organic electroluminescent display, and displays a video or a still image imaged by the solid-state image sensor 404. Here, the output unit 412 may also include a sound output device such as a speaker and a headphone. Here, the input unit 414 is, for example, a device for inputting a user's manipulation such as a touch panel and a button and issues manipulation commands for various functions of the electronic device 400 according to the user's manipulation.

The frame memory 416 temporarily stores the video, the still image and the like imaged by the solid-state image sensor 404. In addition, the recording unit 418 records the video, the still image and the like imaged by the solid-state image sensor 404 in a removable storage medium such as a magnetic disk, an optical disc, a magneto optical disc and a semiconductor memory.

The power supply unit 420 appropriately supplies various types of power serving as operating power of the DSP circuit 406, the control unit 408, the output unit 412, the input unit 414, the frame memory 416 and the recording unit 418 to these supply targets.

The electronic device 400 to which the photoelectric conversion element according to the present technology is applied has been described above. The electronic device 400 to which the photoelectric conversion element according to the present technology is applied may be, for example, an imaging apparatus.

The embodiment(s) of the present disclosure has/have been described above with reference to the accompanying drawings, whilst the present technology is not limited to the above examples. A person skilled in the art may find various alterations and modifications within the scope of the appended claims, and it should be understood that they will naturally come under the technical scope of the present technology.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

<1>

A solid-state image sensor including:
a compound represented by Chemical Formula (1) below,

[Chem. 1]

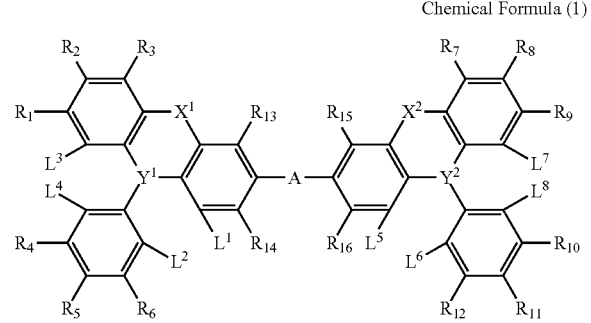

Chemical Formula (1)

in which, in the Chemical Formula (1),

A is a compound formed of an aryl group or a heteroaryl group,

Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

<2>

The solid-state image sensor according to <1>, in which the A has a molecular weight larger than 75.

<3>

The solid-state image sensor according to <1> or <2>, in which a compound represented by the Chemical Formula (1) has a molecular weight larger than 620.

<4>

The solid-state image sensor according to any of <1> to <3>, in which a compound represented by the Chemical Formula (1) has a molecular weight smaller than 1000.

<5>

The solid-state image sensor according to any of <1> to <4>, in which the A includes compounds of Chemical Formula (3) to Chemical Formula (6) below,

[Chem. 3]

Chemical Formula (3)

[Chem. 4]

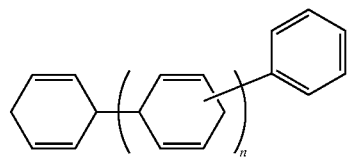

Chemical Formula (4)

[Chem. 5]

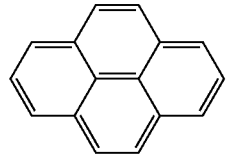

Chemical Formula (5)

[Chem. 6]

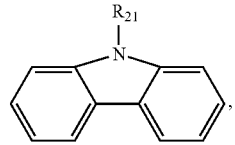

Chemical Formula (6)

B of the Chemical Formula (3) is different from A in Chemical Formula (1), and each represents a carbon atom or a nitrogen atom, n in the Chemical Formula (4) is n=1 to 5, and R21 of the Chemical Formula (6) is aryl group or a heteroaryl group.

<6>
The solid-state image sensor according to <1>,
in which the compound represented by the Chemical Formula (1) includes a compound of Chemical Formula (9) below,

[Chem. 9]

Chemical Formula (9)

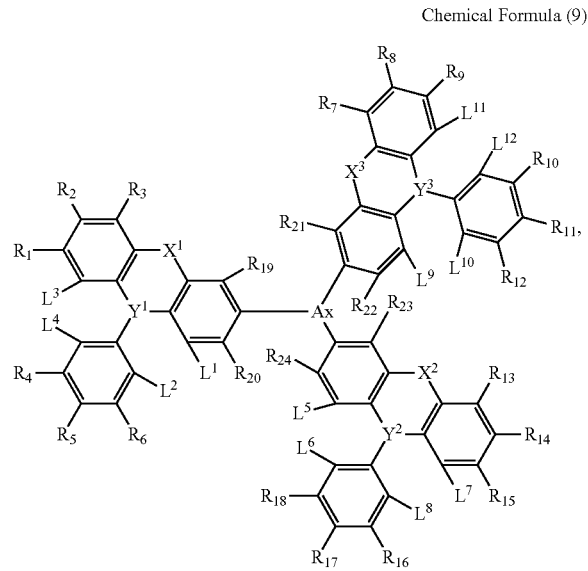

Ax of the Chemical Formula (9) is represented by Chemical Formula (3) below,

[Chem. 3]

Chemical Formula (3)

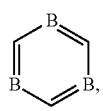

and
B of the Chemical Formula (3) is different from A in Chemical Formula (1), and each represents a carbon atom or a nitrogen atom.
<7>
The solid-state image sensor according to any of <1> to <6>,
in which a layer stacked between a pair of electrodes is configured with a compound of the Chemical Formula (1).
<8>
The solid-state image sensor according to <7>,
further including, between the pair of electrodes:
a photoelectric conversion layer configured to photoelectrically convert incident light; and
an electron blocking layer configured to block an electron for the photoelectric conversion layer,
in which the electron blocking layer is configured with a compound of the Chemical Formula (1).
<9>
The solid-state image sensor according to <8>,
in which the photoelectric conversion layer photoelectrically converts green light.
<10>
A photoelectric conversion film including:
a compound represented by Chemical Formula (1) below,

[Chem. 1]

Chemical Formula (1)

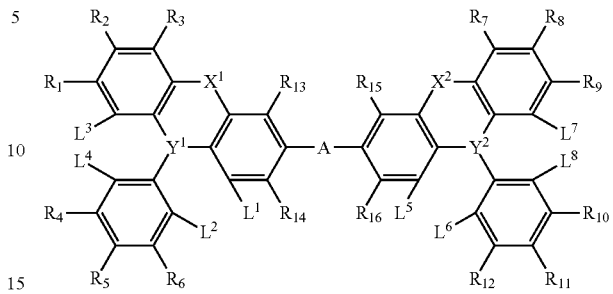

in which, in the Chemical Formula (1),
A is a compound formed of an aryl group or a heteroaryl group,
Y1 and Y2 represent a linker that links via one atom selected from the group consisting of a nitrogen atom, a boron atom, and a phosphorus atom,
X1 and X2 represent a linker that links via one atom selected from the group consisting of an oxygen atom, a sulfur atom, a carbon atom, a nitrogen atom, a phosphorus atom, and a silicon atom,
one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom,
one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and
each of R1 to R16 represents an independent hydrogen atom or a linker that links via one atom selected from the group consisting of substituents other than a hydrogen atom.
<11>
An electron blocking layer including:
a compound represented by Chemical Formula (1) below,

[Chem. 1]

Chemical Formula (1)

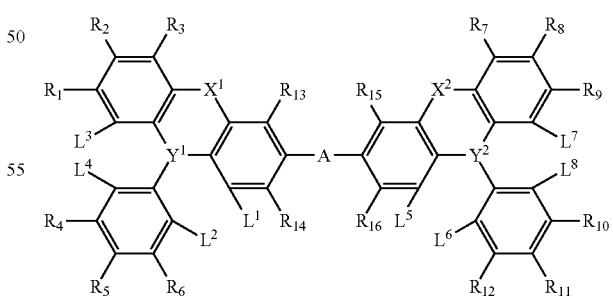

in which, in the Chemical Formula (1),
A is a compound formed of an aryl group or a heteroaryl group,
Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

<12>

An imaging apparatus including:

a compound represented by Chemical Formula (1) below,

[Chem. 1]

Chemical Formula (1)

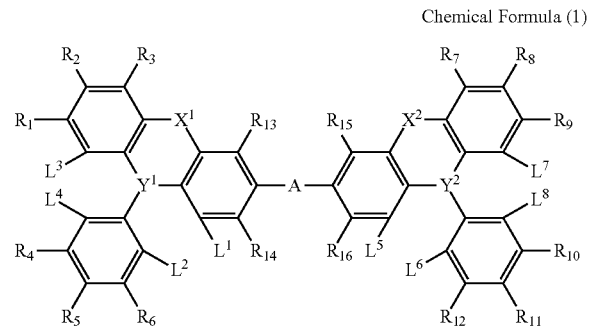

in which, in the Chemical Formula (1),

A is a compound formed of an aryl group or a heteroaryl group,

Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

<13>

An electronic device including:

a compound represented by Chemical Formula (1) below,

[Chem. 1]

Chemical Formula (1)

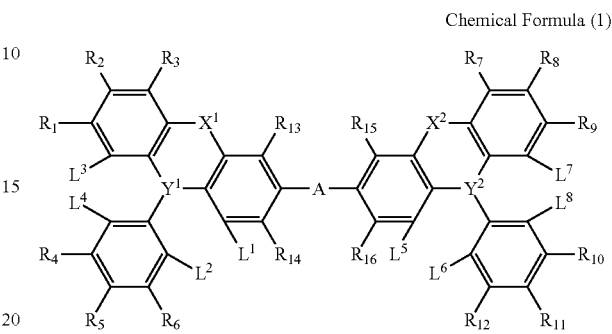

in which, in the Chemical Formula (1),

A is a compound formed of an aryl group or a heteroaryl group,

Y1 and Y2 represent a linker that links via one atom selected from the group consisting of a nitrogen atom, a boron atom, and a phosphorus atom, X1 and X2 represent a linker that links via one atom selected from the group consisting of an oxygen atom, a sulfur atom, a carbon atom, a nitrogen atom, a phosphorus atom, and a silicon atom, one of a set of L1 and L2 and a set of L3 and L4 represents a linker that, by binding to each other, links via one atom selected from the group consisting of an oxygen atom, a sulfur atom, a carbon atom, a nitrogen atom, a phosphorus atom, and a silicon atom, one of a set of L5 and L6 and a set of L7 and L8 represents a linker that, by binding to each other, links via one atom selected from the group consisting of an oxygen atom, a sulfur atom, a carbon atom, a nitrogen atom, a phosphorus atom, and a silicon atom, and each of R1 to R16 represents an independent hydrogen atom or a linker that links via one atom selected from the group consisting of substituents other than a hydrogen atom.

REFERENCE SIGNS LIST 101 photoelectric conversion element
102 substrate
104 lower electrode
106 electron blocking layer
108 photoelectric conversion layer
110 hole blocking layer
112 upper electrode layer

The invention claimed is:

1. A solid-state image sensor comprising:
a compound represented by Chemical Formula (1) below,

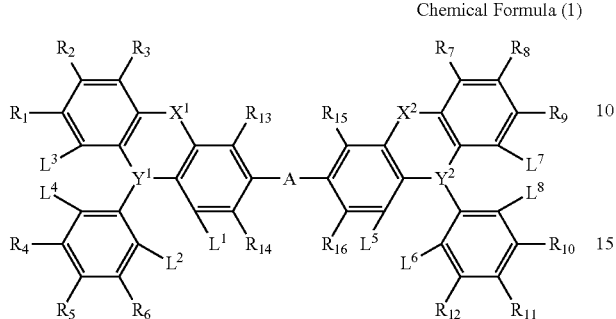

Chemical Formula (1)

wherein, in the Chemical Formula (1),
is a group that comprises one of an aryl group or a heteroaryl group,
Y1 and Y2 represent a first linker that links via a nitrogen atom,
X1 and X2 represent a second linker that links via an oxygen atom,
L3 and L4 represent a third linker that binds the L3 and the L4 to each other, and links via an oxygen atom,
L5 and L6 represent a fourth linker that binds the L5 and the L6 to each other, and links via an oxygen atom,
each of L1, L2, L7, and L8 represents a hydrogen atom, and
each of R1 to R16 represents a hydrogen atom.

2. The solid-state image sensor according to claim 1, wherein the A has a molecular weight greater than 75.

3. The solid-state image sensor according to claim 1, wherein the compound represented by the Chemical Formula (1) has a molecular weight larger than 620.

4. The solid-state image sensor according to claim 1, wherein the compound represented by the Chemical Formula (1) has a molecular weight mailer less than 1000.

5. The solid-state image sensor according to claim 1, wherein
the A comprises a group represented by one of Chemical Formula (3), Chemical Formula (4), Chemical Formula (5), or Chemical Formula (6) below,

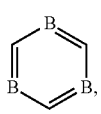

Chemical Formula (3)

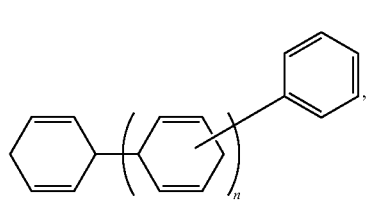

Chemical Formula (4)

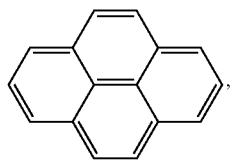

Chemical Formula (5)

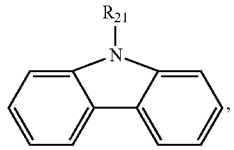

Chemical Formula (6)

each B represents one of a carbon atom or a nitrogen atom,
n in the Chemical Formula (4) is n=1 to 5, and
R21 of the Chemical Formula (6) is one of an aryl group or a heteroaryl group.

6. The solid-state image sensor according to claim 1, wherein
the compound represented by the Chemical Formula (1) is a compound of Chemical Formula (9) below,

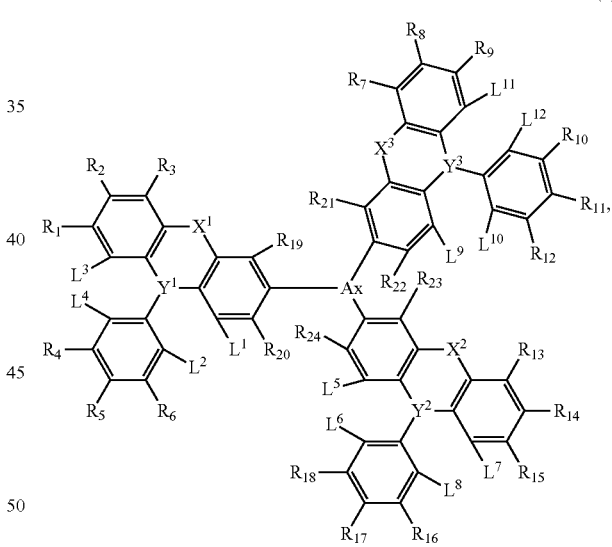

Chemical Formula (9)

Ax of the Chemical Formula (9) is represented by Chemical Formula (3) below,

Chemical Formula (3)

and
B of the Chemical Formula (3) each represents one of a carbon atom or a nitrogen atom.

7. The solid-state image sensor according to claim 1, further comprising:
   a pair of electrodes; and
   a layer, wherein
      the layer is between the pair of electrodes, and
      the layer comprises the compound of the Chemical Formula (1).

8. The solid-state image sensor according to claim 7, further comprising:
   a photoelectric conversion layer configured to photoelectrically convert incident light, wherein the photoelectric conversion layer is between the pair of electrodes; and
   an electron blocking layer configured to block an electron for the photoelectric conversion layer, wherein the electron blocking layer comprises the compound of the Chemical Formula (1).

9. The solid-state image sensor according to claim 8, wherein the photoelectric conversion layer is further configured to photoelectrically convert green light.

* * * * *